United States Patent
Chomik et al.

(10) Patent No.: US 7,350,663 B2
(45) Date of Patent: Apr. 1, 2008

(54) WASTE STORAGE DEVICE (75) Inventors: Richard S Chomik, Orlando, FL (US); Mark Yoho, Chagrin Falls, OH (US); Leslie Stuart, Larchmont, NY (US); Kim Taek, Edgewater, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 10/477,041

(22) PCT Filed: Apr. 10, 2002

(86) PCT No.: PCT/US02/11021

§ 371 (c)(1), (2), (4) Date: Jan. 5, 2005

(87) PCT Pub. No.: WO02/083525

PCT Pub. Date: Oct. 24, 2002

(65) Prior Publication Data

US 2005/0106706 A1    May 19, 2005

(51) Int. Cl.
B65D 43/26  (2006.01)
B65B 9/10   (2006.01)

(52) U.S. Cl. ............... 220/264; 220/908.1; 220/495.06; 53/567; 53/577; 4/484

(58) Field of Classification Search ........... 220/495.06, 220/264, 263, 908.1, 495.08, 495.1; 53/390, 53/567, 577; 4/484
See application file for complete search history.

(56) References Cited

U.S. PATENT DOCUMENTS

| | | | | |
|---|---|---|---|---|
| 3,321,103 A | * | 5/1967 | Phillips | 141/314 |
| 3,452,368 A | | 7/1969 | Couper | |
| 3,602,924 A | * | 9/1971 | Kneisley | 4/484 |
| 3,665,522 A | * | 5/1972 | Backlund et al. | 4/484 |
| 3,935,692 A | | 2/1976 | Miller | |
| 4,025,969 A | * | 5/1977 | Dahlen | 4/484 |
| 4,519,104 A | * | 5/1985 | Nilsson | 4/484 |
| 4,869,049 A | | 9/1989 | Richards et al. | |
| 5,027,578 A | | 7/1991 | Natterer et al. | |
| 5,125,526 A | | 6/1992 | Sumanis | |
| 5,295,607 A | | 3/1994 | Chang | |
| 5,337,581 A | | 8/1994 | Lott | |
| 5,385,259 A | | 1/1995 | Bernstein et al. | |
| 5,520,303 A | | 5/1996 | Bernstein et al. | |
| 5,535,913 A | | 7/1996 | Asbach et al. | |
| 5,590,512 A | | 1/1997 | Richards et al. | |
| 5,655,680 A | | 8/1997 | Asbach et al. | |
| 5,799,909 A | | 9/1998 | Ziegler | |
| 5,813,200 A | | 9/1998 | Jacoby et al. | |

(Continued)

FOREIGN PATENT DOCUMENTS

EP    0 281 355 A2    9/1988

(Continued)

Primary Examiner—Anthony D. Stashick
Assistant Examiner—James N Smalley
(74) Attorney, Agent, or Firm—Ohlandt, Greeley, Ruggiero & Perle, L.L.P.

(57) ABSTRACT

A container adapted for waste storage is provided. The container has a mechanically operated sealing mechanism that allows a user to seal the waste storage film by depressing an actuator.

8 Claims, 7 Drawing Sheets

U.S. PATENT DOCUMENTS 6,065,272 A    5/2000   Lecomte
6,128,890 A   10/2000   Firth
6,170,240 B1   1/2001   Jocoby et al.
6,719,194 B2 * 4/2004   Richards .................... 232/43.1

FOREIGN PATENT DOCUMENTS

EP    0 281 355 B1   9/1988
WO    WO/9817536     4/1998

* cited by examiner

WASTE STORAGE DEVICE

BACKGROUND OF THE INVENTION

1. Field of the Invention

The present invention relates to a waste storage device or container. More particularly, the present invention relates to a waste storage device having a mechanically operated sealing mechanism.

2. Description of the Prior Art

Waste storage devices for disposal of waste, such as baby diapers, are known. One such device is the Playtex Diaper Genie System®.

In the Diaper Genie System®, a film cartridge having a hole concentrically located therein, is positioned in the container body. The film cartridge has a top surface from which a storage film extends and has a twist ring secured in the concentric hole of the cartridge. The storage film extends from the film cartridge, over and then down through the twist ring, down through the hole in the film cartridge and into the container body. When the user manually opens the lid assembly by hand, a diaper can be inserted through the twist ring and hole in the film cartridge, and in the storage film. The twist ring is then manually rotated by the user's hand, which causes the film cartridge and storage film to rotate, tieing off and sealing the disposed diaper in the storage film. The storage film is continuously fed from the film cartridge.

The device requires the user to rotate the twist ring by hand to seal the storage film. In the present invention, the sealing operation is performed mechanically.

SUMMARY OF THE INVENTION

It is an object of the present invention to provide a waste storage device that has a mechanically operated sealing mechanism.

It is another object of the present invention to provide such a waste storage device that allows a user to operate the sealing mechanism with his or her foot.

The above objects and advantages of the present invention are provided by, and the present invention includes a sealing mechanism for a waste storage container that has a body, a lid and a storage film cartridge positioned in the body with the cartridge having a continuous length of storage film therein. The sealing mechanism has an actuator operably connected to the lid and the cartridge, and actuation of the actuator opens the lid and seals the storage film.

Preferably, the sealing mechanism allows a first actuation of the actuator to open the lid and a second actuation of the actuator to seal the storage film. More preferably, the sealing mechanism further comprises a rack gear operably connected to the actuator, a clutch, and a spring connected to the rack gear. Actuation of the actuator causes the rack gear to move in a first direction against the bias of the spring and release of the actuator causes the rack gear to move in a second direction under the bias of the spring, which causes the clutch to rotate the cartridge.

In another embodiment of the present invention, a locking mechanism is operably connected to the spring and a first actuation of the actuator locks the spring in a compressed position while a second actuation of the actuator unlocks the spring.

Other and further objects, advantages and features of the present invention will be understood by reference to the following.

DETAILED DESCRIPTION OF THE INVENTION

Figure 1:
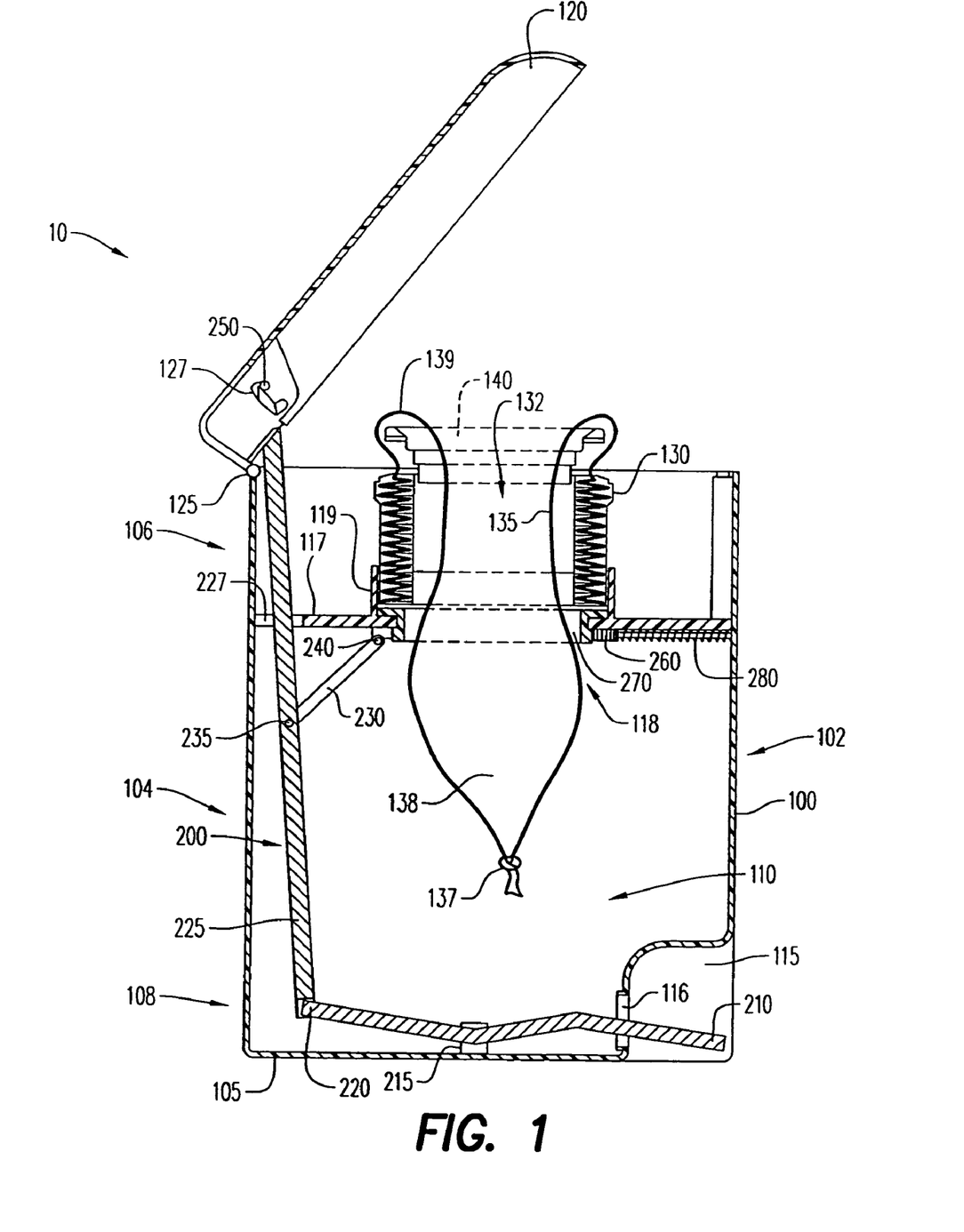
FIG. 1 is a cross-sectional plan view of a waste storage device having the sealing mechanism of the present invention.
Figure 2:
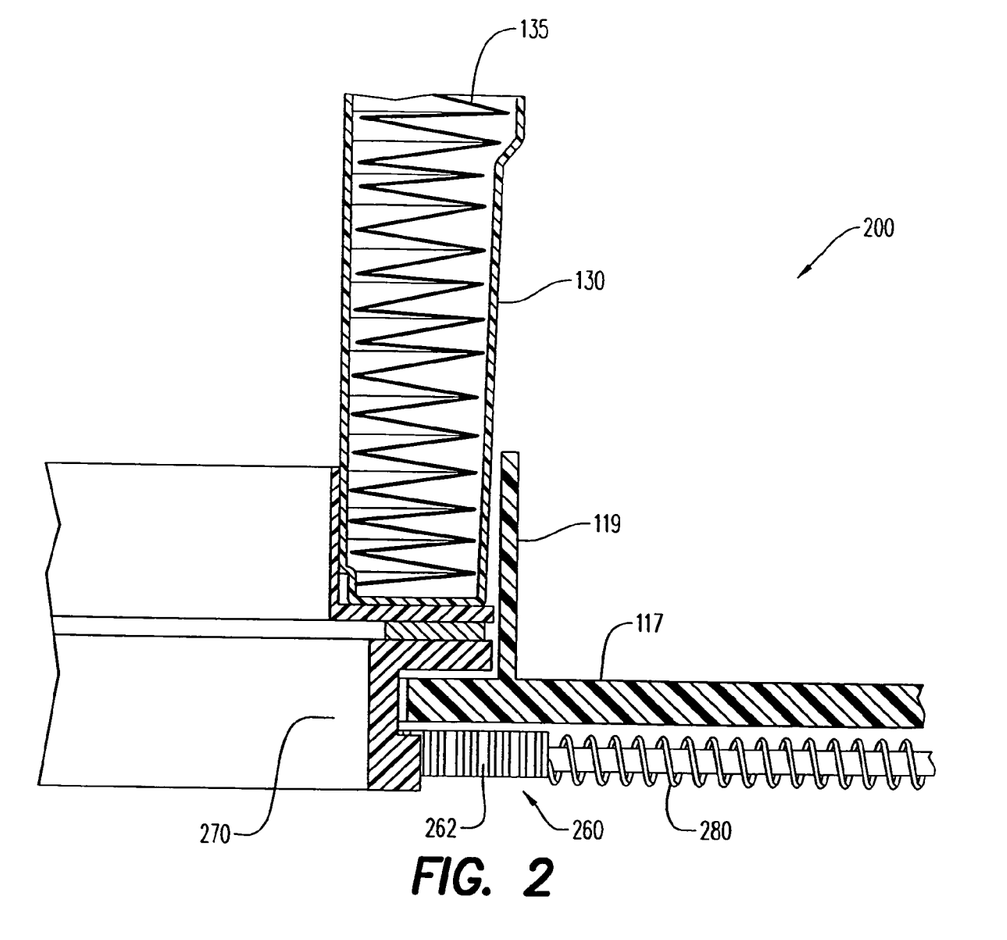
FIG. 2 is a cross-sectional plan view of a portion of the sealing mechanism of FIG. 1.
Figure 3:
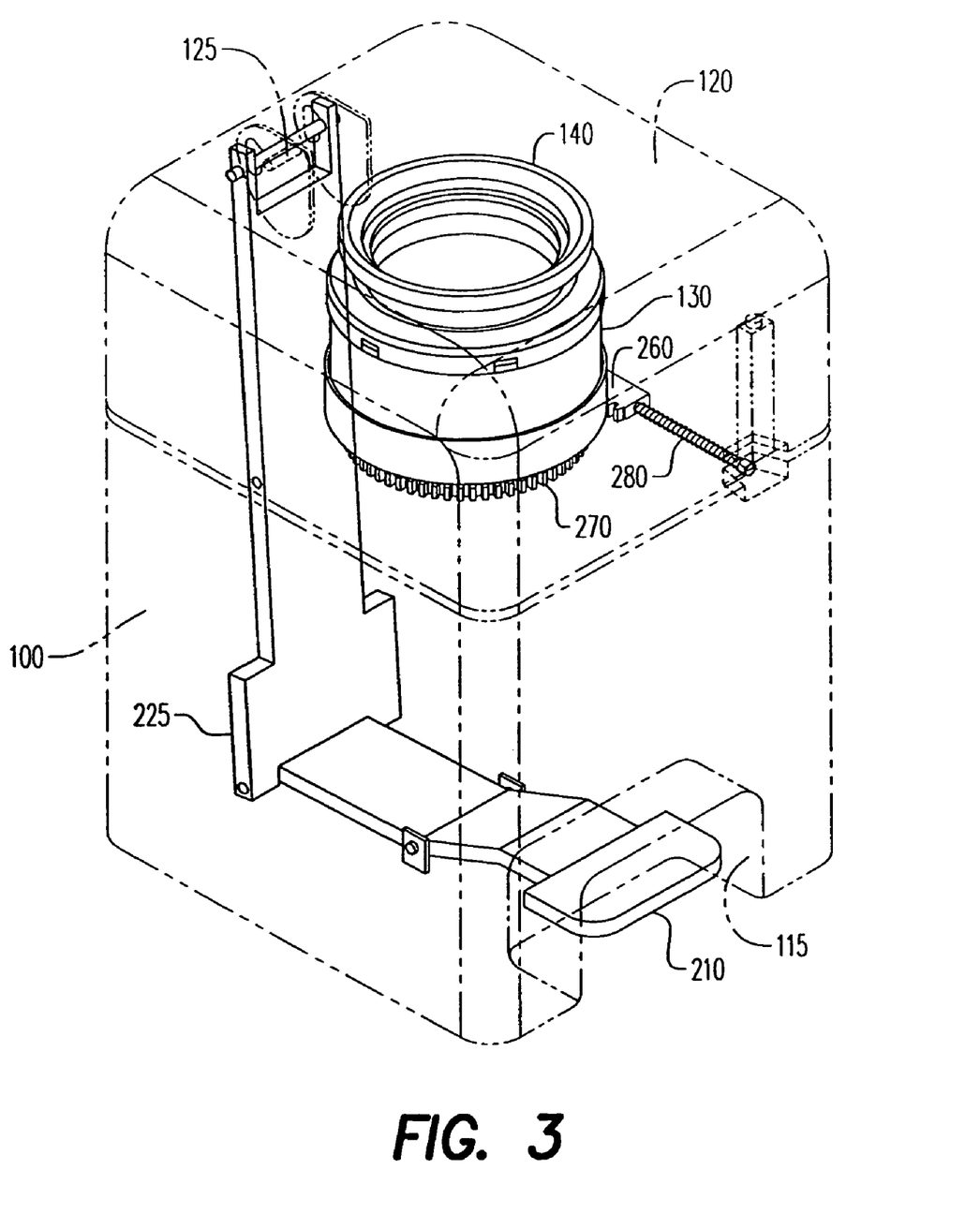
FIG. 3 is a perspective view of the waste storgae device of FIG. 1.
Figure 4:
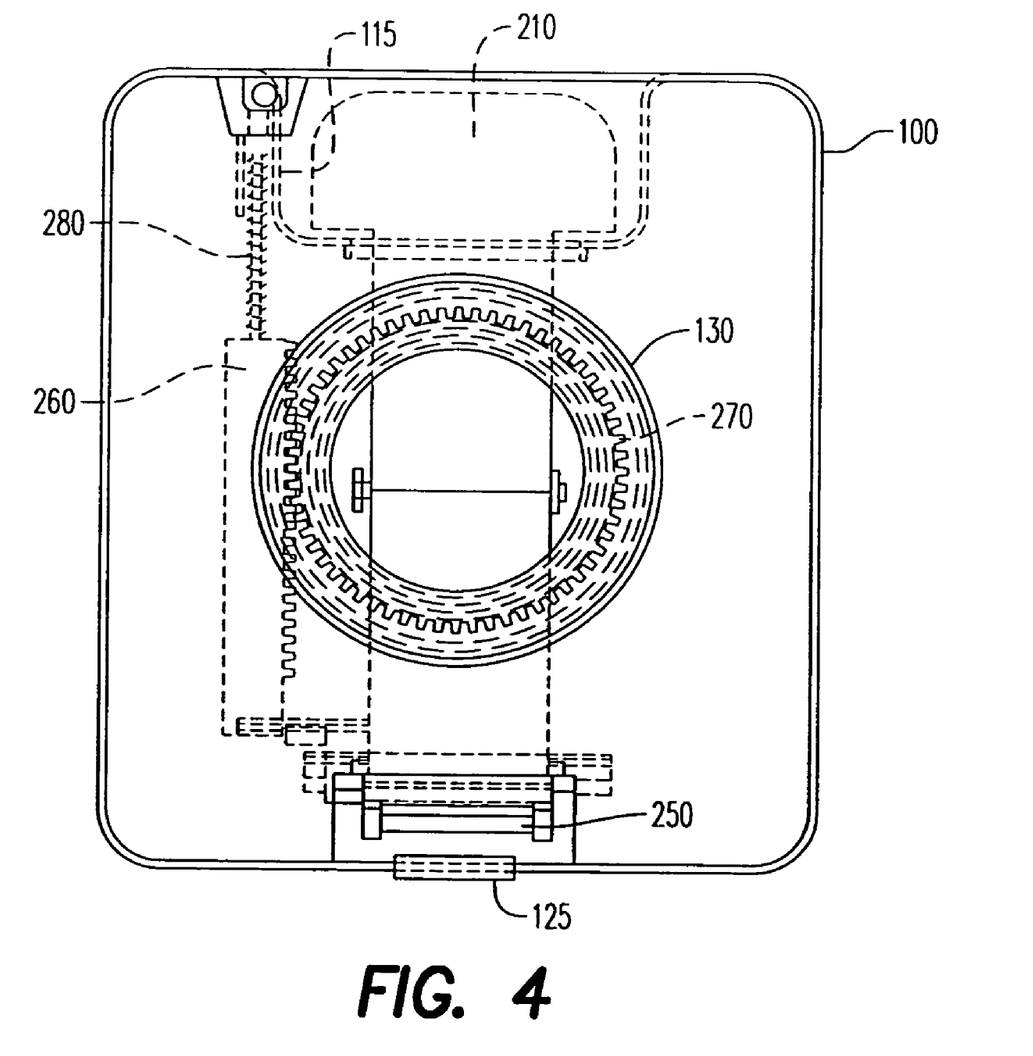
FIG. 4 is a top view of the waste storage device of FIG. 1 without the lid.

Referring to FIG. 1, there is shown a preferred embodiment of a waste storage device having the sealing mechanism of the present invention, generally represented by reference numeral 10.

Waste storage device 10 has a body 100, a lid 120, a storage film cassette 130, a film ring 140 and a sealing mechanism 200. Body 100 has a base 105, an inner volume 110, front and rear portions 102, 104, and upper and lower portions 106, 108. Body 100 is substantially cylindrical in shape to maximize inner volume 110. However, alternative shapes for body 100 can also be used including rectangular or cubical. Lower portion 108 of body 100 has an indentation or pedal housing 115 that will be described later in greater detail. Preferably, pedal housing 115 is positioned along front portion 102.

Lid 120 is substantially cylindrical in shape and has a diameter substantially the same size as the diameter of body 100 to provide a sealing engagement of the lid with the body along upper portion 106. If an alternative shape of body 100 is used, such as rectangular or cubical, then the corresponding shape would also be used for lid 120 to provide a sealing engagement of the lid and the body along upper portion 106. Lid 120 is pivotally connected to body 100 by lid hinge 125. Preferably, lid hinge 125 is positioned along rear portion 104. Lid 120 has a lid slot 127 formed therein. Lid slot 127 is a u-shaped channel that is operably connected to sealing mechanism 200 to allow a user to open and close lid 120, which will be discussed later in greater detail.

Body 100 further has a cassette flange 117 with a center hole 118 and a circular wall 119. Flange 117 is circumferentially formed along the inner wall of body 100 in proximity to upper portion 106. Flange 117 engages with a clutch 270 of sealing mechanism 200, which will be discussed later in greater detail. Center hole 118 provides a support for clutch 270 and for cassette 130, which is seated on the clutch. Circular wall 119 extends substantially vertically upward from flange 117. As used herein, vertical refers to the direction between upper and lower portions 106, 108, which is substantially parallel with the sidewalls defining body 100. Horizontal refers to the direction between front and rear portions 102, 104, which is substantially perpendicular to the sidewalls defining body 100. Circular wall 119 has a diameter larger than the diameter of cassette 130. Circular wall 119 provides support for cassette 130 to prevent it from moving in a horizontal direction yet allowing it to rotate in center hole 118.

Cassette 130 preferably has a cylindrical or ring-like shape with a center opening 132. Film 135 is a continuous sheet of film having a cylindrical shape that is stored in cassette 130. Cassette 130 also has a film ring 140 that is positioned in center opening 132. Film 135 is dispensed from the top of cassette 130 over the outside of film ring 140 and then down through the film ring and down through center opening 132 into inner volume 110. Film 135 is tied off or sealed at lower end 137 of the film in inner volume 110 to provide a storage volume 138. As will be discussed later in greater detail, in the preferred embodiment, after a diaper is inserted in storage volume 138, sealing mechanism 200 rotates cassette 130 to seal film upper end 139.

Referring to FIGS. 1 through 4, sealing mechanism 200 of the present invention is shown. Sealing mechanism 200 has an actuator 210, a foot pedal linkage 225, a rack linkage 230, a rack gear 260, a clutch 270 and a biasing mechanism 280. In the preferred embodiment, actuator 210 is a foot pedal and is angled downward for facilitating operation by a user's foot. Pedal 210 protrudes out from body 100 through pedal orifice 116 and into pedal housing 115. Pedal housing 115 has a height that allows a user to slide his or her foot into the housing and onto pedal 210. Pedal 210 is pivotally connected to base 105 of body 100 at pedal pivot 215. This pivotal connection translates the user's downward force into an upward force for opening lid 120.

Pedal 210 is pivotally connected to foot pedal linkage 225 at pedal linkage pivot 220. This pivotal connection translates the rotational movement of pedal 210 into a substantially vertical movement of pedal linkage 225. Pedal linkage 225 extends substantially vertically from lower portion 108 of body 100, through flange opening 227, through upper portion 106 of body 100, to lid 120. Pedal linkage 225 is pivotally secured to lid 120 such that an upward force along the pedal linkage causes the lid to rotate about lid hinge 125.

In this embodiment, pedal linkage 225 is operably connected to lid 120 by lid slot 127 and lid tongue 250. Lid slot 127 is preferably a u-shaped channel formed in lid 120. Lid tongue 250 is preferably a cylindrical tongue that engages with lid slot 127. Preferably, lid tongue 250 has a cap to secure the tongue in lid slot 127.

Pedal linkage 225 is also pivotally connected to rack linkage 230 at rack pivot 235. Rack linkage 230 is pivotally connected to rack gear 260 at rack pivot 240. The pivotal connections at rack pivots 235, 240 translate the substantially vertical movement of pedal linkage 225 into a substantially horizontal movement of rack linkage 230 and rack gear 260.

Rack gear 260 is operably connected to clutch 270 so that a horizontal movement of the rack gear causes the clutch to rotate. In this embodiment, clutch 270 has gears (not shown) that engage with gears 262 of rack gear 260. Rack gear 260 is further connected to a biasing mechanism 280 positioned on the opposite end of the rack gear from rack pivot 240. In this embodiment, biasing mechanism 280 is a coil spring that biases rack gear 260 toward rear portion 104 of body 100.

Clutch 270 is removably connected to cartridge 130. Clutch 270 is a one-way clutch that only permits rotation of cartridge 130 in one direction. Thus, rack gear 260 can horizontally move in two directions and clutch 270 can rotationally move in two directions. However, cassette 130 can only rotate in one direction.

In operation, when a user depresses pedal 210, pedal linkage 225 moves in an upward direction. This upward movement of pedal linkage 225 causes lid 120 to rotate about lid hinge 125 toward rear portion 104 of body 100. Thus, depressing pedal 210 causes the lid to open.

Simultaneously, the upward movement of pedal linkage 225 causes rack linkage 230 to move substantially horizontally toward front portion 102 of body 100. This causes rack gear 260 to move horizontally toward front portion 102. Rack gear 260 is operably connected to clutch 270, which causes the clutch to rotate in a first direction. Cassette 130 remains stationary because clutch 270 is a one-way clutch and prevents the cassette from rotating in this first direction. The horizontal movement of rack gear 260 towards front portion 102 also causes spring 280 to compress.

With lid 120 in an open position and storage volume 138 accessible to the user, waste storage, such as a diaper, can be inserted through film ring 140 into the storage volume. The user then releases pedal 210 to commence the sealing operation. The force of compressed spring 280 against rack gear 260 causes the rack gear to horizontally move back toward rear portion 104. The horizontal movement of rack gear 260 toward rear portion 104 causes clutch 270 to rotate in a second, opposite direction. Cassette 130 rotates in this second direction. The rotation of cassette 130 causes film 135 to tie off or seal near film upper end 139. Thus, release of pedal 210 causes sealing mechanism 200 to seal film 135.

Simultaneously, the horizontal movement of rack gear 260 toward rear portion 104 causes rack linkage 230 to move toward rear portion 104. The horizontal movement of rack linkage 230 toward rear portion 104 causes movement of pedal linkage 225 in a substantially downward direction toward base 105. The movement of pedal linkage 225 in a substantially downward direction causes lid 120 to rotate about lid hinge 125 toward front portion 102. Thus, release of pedal 210 causes sealing mechanism to close lid 120.

Figure 5:
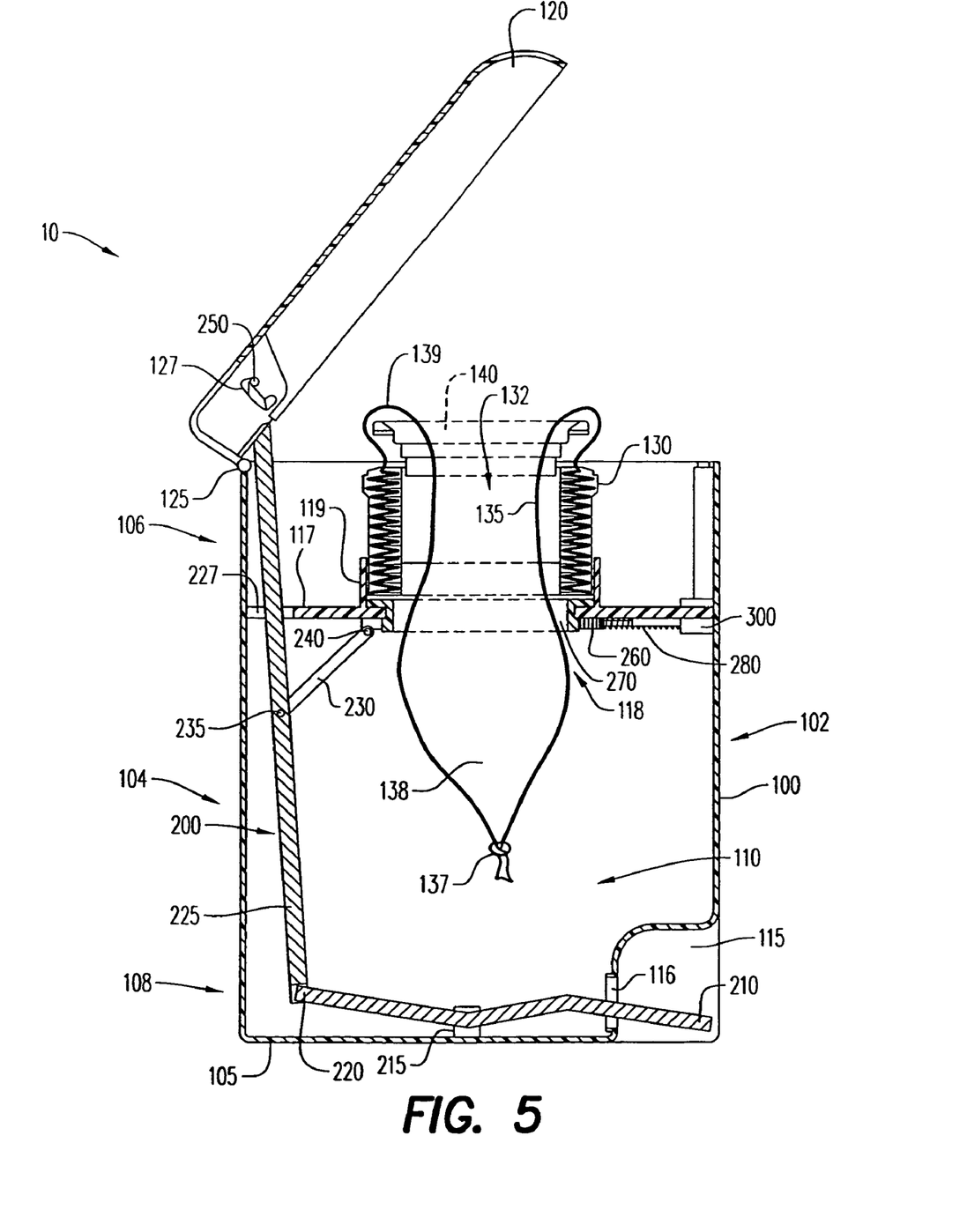
FIG. 5 is a cross-sectional plan view of a waste storage device having a second embodiment of the sealing mechanism of the present invention.
Figure 6:
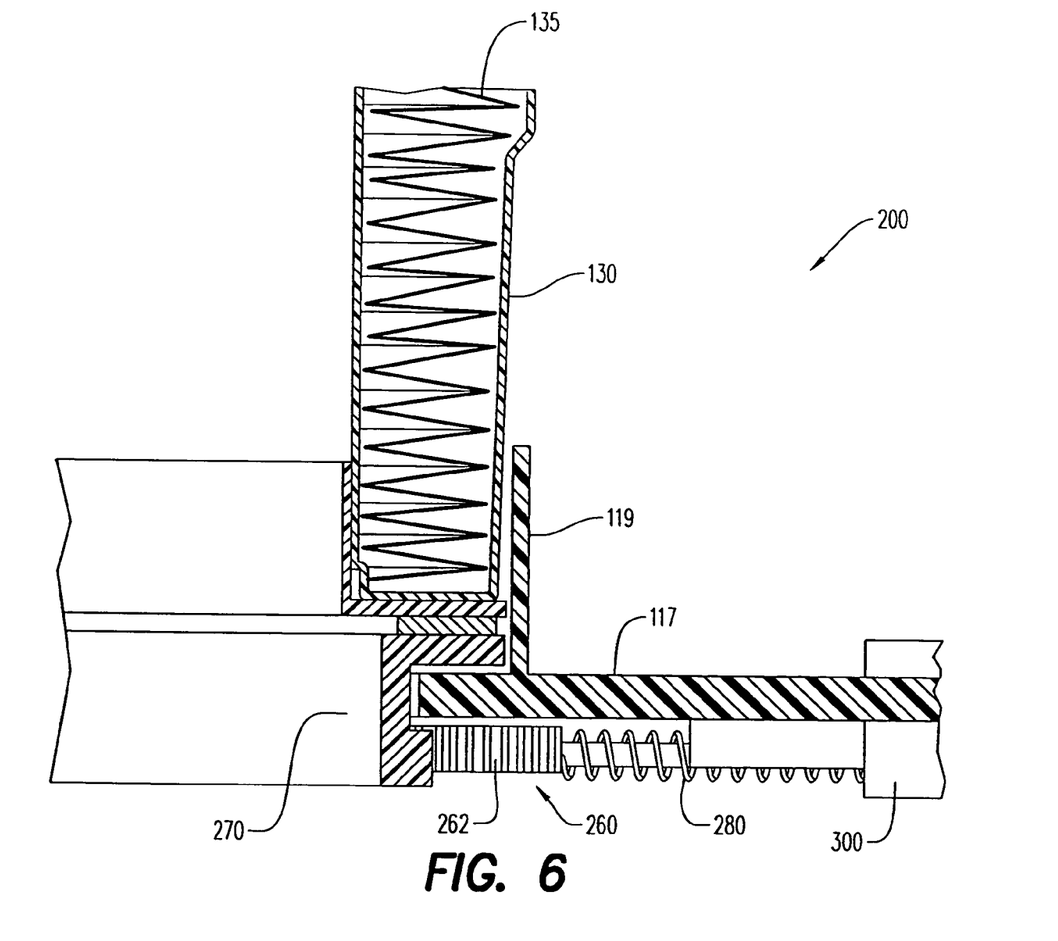
FIG. 6 is a cross-sectional plan view of a portion of the sealing mechanism of FIG. 3.
Figure 7:
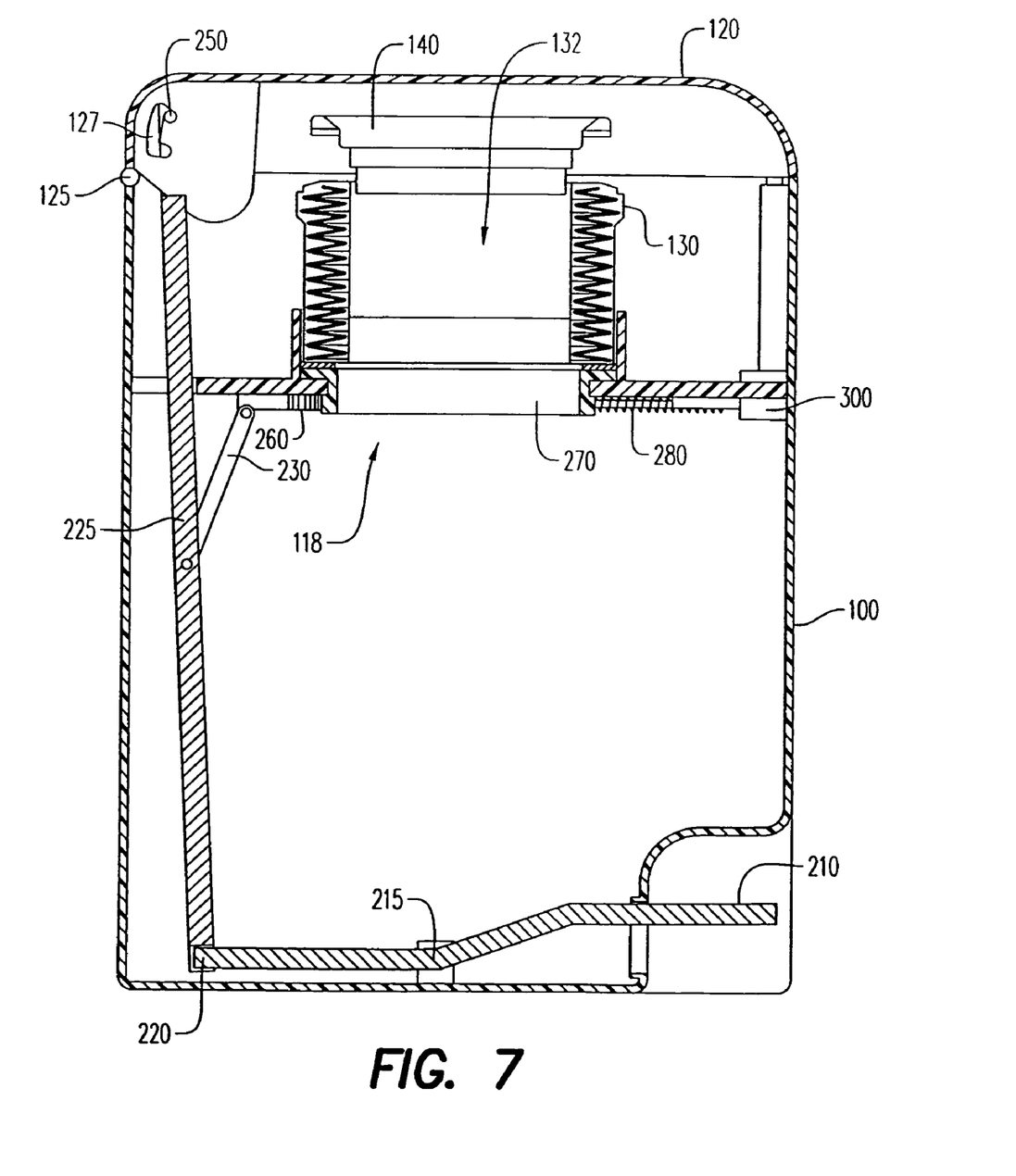
FIG. 7 is a cross-sectional plan view of the waste storage device of FIG. 5 with the lid closed.

Referring to FIGS. 5 through 7, in an alternative embodiment, sealing mechanism 200 also has a locking mechanism 300. Locking mechanism 300 is operably connected to spring 280. When a user first actuates pedal 210 causing rack gear 260 to move toward front portion 102 and compressing spring 280, locking mechanism 300 is triggered and locks spring 280 in a compressed position. Thus, lid 120 remains in an open position and a user can release his or her foot from pedal 210. When a user actuates pedal 210 for a second time causing rack gear 260 to move further toward front portion 102 and further compressing spring 280, locking mechanism 300 is again triggered and unlocks spring 280 from a compressed position. Rack gear 260 is moved back toward rear portion 104 under the force of spring 280 causing rotation of clutch 270 and cassette 130, as well as downward movement of pedal linkage 225. Thus, film 135 is sealed by the rotation of cassette 130 and lid 120 is closed by the downward movement of pedal linkage 225. Pedal 210 returns to its upper position for the sealing operation to be repeated by a first and second downward depression of the pedal.

The present invention having thus been described with particular reference to the preferred forms thereof, it will be obvious that various changes and modifications may be made therein without departing from the spirit and scope of the present invention as defined in the appended claims.

What is claimed is:

1. A sealing mechanism for a waste storage container, said waste storage container having a body, a lid and a storage film cartridge adapted to be positioned in said body, said cartridge having a continuous length of storage film therein, said sealing mechanism comprising:

an actuator operably connected to said lid and said cartridge, wherein actuation of said actuator opens said lid and seals said storage film, and wherein said actuator rotates said cartridge in only one direction causing said storage film to seal;

a clutch operably connected to said actuator and said cartridge, said clutch allowing said cartridge to rotate in only one direction; and a rack gear operably connected to said actuator and said clutch, and a spring connected to said rack gear, wherein actuation of said actuator causes said rack gear to move in a first direction against the bias of said spring and release of said actuator causes said rack gear to move in a second direction under the bias of said spring to cause said clutch to rotate said cartridge.

2. The sealing mechanism of claim 1, wherein said actuator has a first actuation that opens said lid and a second actuation of said actuator that seals said storage film.

3. The sealing mechanism of claim 2, wherein said second actuation of said actuator closes said lid.

4. The sealing mechanism of claim 1, wherein said actuator is operably connected to said cartridge by at least one linkage.

5. The sealing mechanism of claim 4, wherein said body has a bottom, and wherein said actuator is positioned substantially near the bottom of said body.

6. The sealing mechanism of claim 5, wherein said actuator protrudes from said body.

7. The sealing mechanism of claim 5, wherein said actuator is pivotally connected to a first linkage and said first linkage is pivotally connected to a second linkage, wherein said first linkage is operably connected to said lid to allow a user to open and close said lid and said second linkage is operably connected to said cartridge to allow a user to seal said storage film.

8. A sealing mechanism for a waste storage container, said waste storage container having a body, a lid and a storage film cartridge adapted to be positioned in said body, said cartridge having a continuous length of storage film therein, said sealing mechanism comprising:

an actuator operably connected to said lid and said cartridge, wherein actuation of said actuator opens said lid and seals said storage film, and wherein said actuator rotates said cartridge in only one direction causing said storage film to seal;

a clutch operably connected to said actuator and said cartridge, said clutch allowing said cartridge to rotate in only one direction;

a rack gear operably connected to said actuator and said clutch, and a spring connected to said rack gear, wherein actuation of said actuator causes said rack gear to move in a first direction against the bias of said spring and release of said actuator causes said rack gear to move in a second direction under the bias of said spring to cause said clutch to rotate said cartridge; and a locking mechanism operably connected to said spring, wherein said actuator locks said spring in a compressed position upon a first actuation and said actuator unlocks said spring upon a second actuation.

\* \* \* \* \*